United States Patent
Nordbryhn

[19]
[11] Patent Number: 5,898,169
[45] Date of Patent: *Apr. 27, 1999

[54] DEVICE FOR GENERATING, DETECTING AND RECOGNIZING A CONTOUR IMAGE OF A LIQUID CONTAINER

[75] Inventor: Andreas Nordbryhn, Oslo, Norway

[73] Assignee: Tomra Systems A/S, Asker, Norway

[*] Notice: This patent issued on a continued prosecution application filed under 37 CFR 1.53(d), and is subject to the twenty year patent term provisions of 35 U.S.C. 154(a)(2).

[21] Appl. No.: 08/601,257

[22] Filed: Feb. 14, 1996

Related U.S. Application Data

[63] Continuation-in-part of application No. 08/221,106, Mar. 31, 1994, abandoned.

[51] Int. Cl.[6] .............................. G01N 9/04; G01N 21/90
[52] U.S. Cl. ...................................... 250/223 B; 356/240
[58] Field of Search ........................ 250/223 B; 209/522, 209/523, 524, 525, 529; 356/376, 239, 240

[56] References Cited

U.S. PATENT DOCUMENTS

| | | |
|---|---|---|
| 4,074,808 | 2/1978 | Gillespie et al. . |
| 4,097,158 | 6/1978 | Dehait ..................................... 356/387 |
| 4,577,969 | 3/1986 | Tagaya et al. . |
| 4,610,542 | 9/1986 | Ringlien ............................. 250/223 B |
| 4,664,525 | 5/1987 | Tagaya et al. . |
| 4,786,801 | 11/1988 | Shay . |
| 4,859,862 | 8/1989 | Planke et al. . |
| 4,906,098 | 3/1990 | Thomas et al. . |
| 5,110,213 | 5/1992 | Seymour ................................ 356/445 |
| 5,233,186 | 8/1993 | Ringlien ............................. 250/223 B |
| 5,280,170 | 1/1994 | Baldwin et al. . |

FOREIGN PATENT DOCUMENTS

| | | |
|---|---|---|
| 1521406 | 8/1978 | Germany . |
| 2065299 | 1/1981 | United Kingdom . |
| 2157824 | 10/1985 | United Kingdom . |

*Primary Examiner*—Edward P. Westin
*Assistant Examiner*—Kevin Pyo
*Attorney, Agent, or Firm*—Rodman & Rodman

[57] ABSTRACT

A device for generating, detecting and recognizing a contour image of a liquid container, such as at least partly transparent, colored or non-colored bottles comprising a light source, light detector means, means for directing light rays received from said light source as parallel rays transversely of a path travelled by said container, and for conveying to said light detector means light rays which are not refracted or hidden by said container, processing means connected to said light detector means for processing signals from said detector means which are indicative of such detected light rays, and means for comparing such processed signals with predetermined container feature data to recognize said contour image of the container. The means for directing light rays suitably comprises a Fresnel lens which is located at a longitudinal side of said path, and a planar mirror located at an opposite longitudinal side of said path, said light source e.g. being a stationary light emitting diode capable of emitting light towards a lens. Said light detector means is suitably a TV camera, e.g. of the CCD type capable of detecting a container contour highlighted by light not hidden or refracted by the container.

9 Claims, 5 Drawing Sheets

DEVICE FOR GENERATING, DETECTING AND RECOGNIZING A CONTOUR IMAGE OF A LIQUID CONTAINER

This application is a continuation in part of application Ser. No. 08/221,106 filed Mar. 31, 1994 and now abandoned.

The present invention relates to a device for generating, detecting and recognizing a contour image of a liquid container, such as at least partly transparent, coloured or non-coloured bottles.

In the prior art there are known several ways and means for generating, detecting and characterizing an image of liquid containers. However, problems are often met when trying to make images of liquid containers, such as bottles, in order to present the shape of such container. Materials like glass and plastics both reflect and convey light, in a way to cause the shape of the article not to be properly shown by an imaging system.

U.S. Pat. No. 4,859,862 (Planke et al), issued Aug. 22, 1989, relates to a light source, means for directing light rays received from light source as parallel rays transversely of a path travelled by a liquid container, light reflective means for receiving such parallel light rays which are not refracted or hidden by said container, and retro-reflecting such received parallel light rays back transversely of said path and through said directing means, said means for directing light rays being a single light path controlling means located at a first longitudinal side of said path, and said light retro-reflective means being located at a second longitudinal side of said path. Inclined mirror leans can be provided, according to said U.S. Pat. No. 4,859,862 for receiving and redirecting said reflected light rays which leave said directing means. Light detector means are arranged for receiving the redirected light, and processing means are connected to the light detector means for processing signals from the detector means which are indicative of such detected light rays. Further, means are provided for comparing such processed signals with predetermined container feature data to recognize the contour image of the container. According to the prior art the light source is suitably a laser beam directed towards a rotary mirror to cause the laser beam to scan the light towards a collimating optical element, e.g. a holographic element.

A further example of the prior art for generating, detecting and recognizing a contour image of a liquid container is described in U.S. Pat. No. 4,625,107 (Planke), issued Nov. 25, 1986. That patent refers to a method for contour recognition of totally or partly transparent objects, e.g. bottles, where the object is advanced through an illumination and detector station and there being illuminated on at least part of its circumference. The light reflected by the object is viewed by a detector against a background that is dark relative to the object, and the viewed image is recorded and converted to pulse signals that are processed to yield a numerical code characteristic of the object. The method requires a particular positioning of light sources to avoid the light sources being directly viewable by a TV camera, e.g. a CCD camera.

As an even further, but not so relevant example of the prior art, U.S. Pat. No. 4,786,801 (Shay) describes an apparatus for testing the sealability of the mouth of a container. Means are provided for in a downward direction vertically displacing a mirror means from a location vertically above the bottle to be inspected to a position whereat a portion of said mirror means is to be located within the bottle during inspection, whereby a portion of said horizontal light beam will pass through one wall of the bottle and the retaining portion will pass above the bottle. A collimated ant intense light beam is used and the bottle is rotated while the mirror means is located within the bottle at the neck/mouth portion thereof.

Contrary to the present invention which intends to let the container pass in an uninterrupted movement when inspected, SHAY requires that the mirror shifting the vertical rays into horizontal rays must be placed inside the bottle. Otherwise, there is no way of inspecting the circumference of the bottle mouth as the bottle rotates. Thus, the SHAY device requires the bottle to stop on the conveyor, the mirror to be lowered into the bottle mouth, the bottle to be turned and the mirror to be removed before the next bottle can be inspected. Perfect alignment must be made of the bottle; if not, then damage to the mirror may easily occur. SHAY is therefore related to a device which is time-consuming to use per bottle detected.

The present invention, however aims at providing a device which generates, detects and recognizes a more correct contour image of a liquid container than that which has been previously obtainable.

In a first embodiment of the present invention, there is provided a device for generating, detecting and recognizing a contour image of a liquid container, comprising a stationary light source, light detector means, means for conveying said container in a substantially continuous motion along a path, means for directing light rays received from said light source as parallel rays transversely of the path travelled by said container, said light detector means receiving those light rays which are not refracted or hidden by said container, said means for directing light rays being first and second lenses, preferably Fresnel lenses, coaxially and respectively located at opposite longitudinal sides of Said path, said light source capable of emitting light towards said first lens, and said light detector means being a TV camera capable of detecting a container contour highlighted by light not refracted or hidden by the container, processing means connected to said light detector means for processing signals from said detector means which are indicative of such detected light rays, and means for comparing such processed signals with predetermined container feature data to recognize said contour image of the container.

According to further features of the device, a first mirror is located at an angle, e.g. 45°, to a common central axis through said Fresnel lenses to convey light between said light source and said first Fresnel lens. Further, a second mirror may be located at an angle, e.g 45°, to a common central axis through said Fresnel lenses to convey light not refracted or hidden by said container between said second Fresnel lens and said camera.

According to a second embodiment of the present invention, there is provided a device for generating, detecting and recognizing a contour image of a liquid container, comprising:

a stationary light source, light detector means, means for conveying said container in a substantially continues motion along a path, means for directing light rays received from said light source of the path travelled by said container, a retro-reflective means for receiving those of such light rays which are rot refracted or hidden by said container, said retro-reflective means reflecting such light rays back through said directing means, inclined mirror means for receiving said retro-reflected light rays leaving said directing means and redirecting said light rays to said light detector means, processing means connected to said light detector means for processing signals from said detector means which are indicative of such detected light rays, said means for directing light rays being first and second lenses, preferably Fresnel lenses, coaxially and respectively located at opposite longitudinal sides of said path, said light source capable of emitting light towards said first lens, and said light detector means being a TV camera capable of detecting a container contour highlighted by light not refracted or hidden by the container, processing means connected to said light detector means for processing signals from said detector means which are indicative of such detected light rays, and means for comparing such processed signals with predetermined container feature data to recognize said contour image of a container.

According to a third and preferred embodiment of the present invention, there is provided a device for generating, detecting and recognizing a contour image of a liquid container, comprising:

a stationary light source, means for directing light rays received from said light source as parallel rays transversely of the path travelled by said container, light reflective means for receiving such parallel light rays which are not refracted or hidden by said container, and reflecting such received parallel light rays back as parallel rays transversely of said path and through said directing means, said means for directing light rays being a single lens, preferably a Fresnel lens, located at a first longitudinal side of said path, and said light reflective means being located at a second longitudinal side of said path, inclined mirror Sears for receiving and redirecting said reflected light rays passing through said lens, light detector Pears for receiving said redirected light, said light detector means being a TV camera capable of detecting a container contour highlighted by light not refracted or hidden by the container, processing means connected to said light detector means for processing signals from said detector means which are indicative of such detected light rays, and means for comparing such processed signals with predetermined container feature data to recognize said contour image of a container.

According to a further feature of said third embodiment of the present device, said light reflective element is a planar mirror.

According to a fourth embodiment of the present invention there is provided a device for generating, detecting and recognizing a contour image of a liquid container, comprising:

a stationary light source, light detector means, means for conveying said container in a substantially continuous motion along a path, means for directing light rays received from said light source as parallel rays transversely of the path travelled by said container, a retro-reflective means for receiving those of such light rays which are not refracted or hidden by said container, said retro-reflective means reflecting such light rays back through said directing means, inclined mirror means for receiving said retro-reflected light rays leaving said directing means and redirecting said light rays to said light detector means, processing means connected to said light detector means for processing signals from said detector means which are indicative of such detected light rays, said means for directing light rays being a single lens, preferably a Fresnel lens, located at a first longitudinal side of said path, and said retro-reflective means being located at a second longitudinal side of said path, said light source capable of emitting light towards said lens, and said light detector means being a TV camera capable of detecting a container contour highlighted by light not refracted or hidden by the container, processing means connected to said light detector means for processing signals from said detector means which are indicative of such detected light rays, and means for comparing such processed signals with predetermined container feature data to recognize said contour image of a container.

According to said first, second, third and fourth embodiments and in order to create parallel rays across said path, said light source is a point size light scattering light source located at a focal point of the lens adjacent said light source.

According to said second and fourth embodiments using retro-reflective means, said light source is a point size light scattering light source located outside a focal point of the lens adjacent said light source, the rays across said path thus not being parallel.

According to further features of said first, second, third and fourth embodiments, said light source is elected from the group of a light emitting diode; an incadescent lamp; arc lamp means; and a laser source having light diffusor means. Suitably said light source is a pulsed light source.

Means may be provided for synchronizing operation of said light source with container location relative to said lenses, or means for pulsing said light source syncronously to camera image frequency.

Preferably said TV camera is a CCD camera.

The device may also comprise means for enabling said container path of travel to be a free fall path which is in particular useful when the liquid container is conveyed downward, e.g. from one floor to a floor below. It is then also possible to obtain an image of the lowermost part of the container.

In connection with said second, third and fourth embodiments, said inclined, mirror means is a semi-transparent mirror capable of passing through light rays emitted by said light source towards said lens.

It is also possible, in particular when using a lens or lenses of Fresnel lens type, to let the lens have a rectangular shape.

Further features of the present invention will appear from the attached patent claims as well as from the following description of the preferred, non-limitative embodiments of the present invention.

The present invention is now to be described further with reference to the following description and the enclosed drawing figures.

Figure 1:
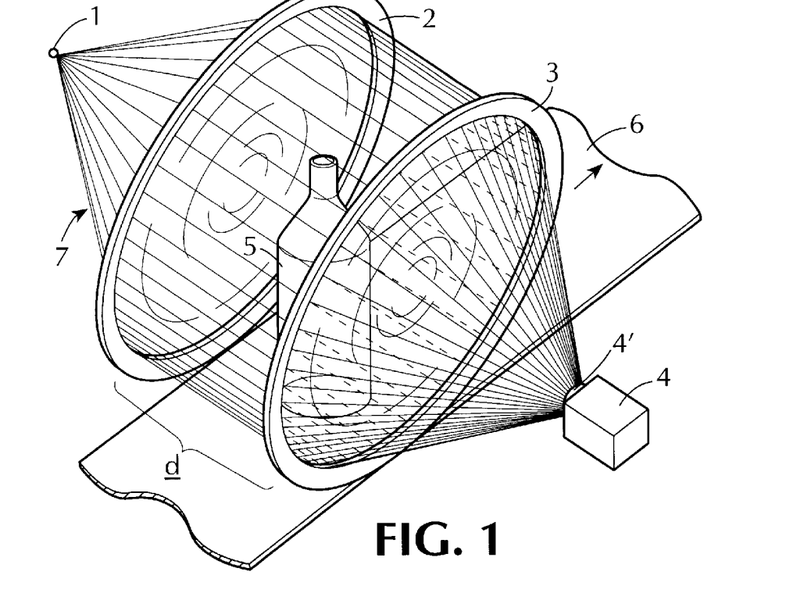
FIG. 1 shows a first embodiment of the device according to the present invention.

In the novel first embodiment of the invention, as shown in FIG. 1 the illumination system for contour imaging of bottles and other liquid containers consists of a light source 1, suitably a point size light scattering light source, and suitably elected from the group of: a light emitting diode; an incadescent lamp, an arc lamp; and a laser source having light diffusor means, two large lenses 2, 3 and a camera 4. The lenses are preferably of the Fresnel lens type providing relatively flat, low cost lenses. Further, such lens type is in particular suitable for large area inspection or inspection of bottles, typically being of a height in the range of 400 mm or more. A liquid container 5, e.g. a bottle is caused by means of conveyor means 6 to travel past the said lenses 2, 3 in the space therebetween. In FIG. 1 the light rays are, for the purpose of the illustration indicated by a plurality of solid lines 7. The center of the light source 1 is located at the focal plane and on the optical axis of the lens 2. The two lenses 2, 3 have aligned, merging optical axes, and with a spacing d therebetween which is wide enough to let objects like liquid containers pass between said lenses. The liquid container 5 is caused to pass between the two lenses 2, 3 and the camera 4 is positioned to let the camera lens lie in the focal plane and centered on the optical axis of the lens 3. Thus, the small light source 1 and the lens 4' of the camera 4 are located on the same optical axis.

Figure 6:
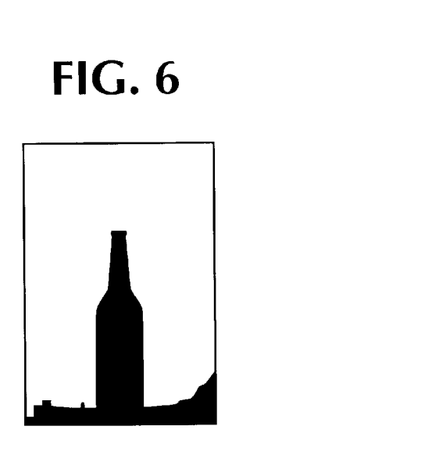
FIG. 6 is a test picture of an image of a bottle generated and detected according to the principles of the embodiment of FIG. 1.

The image viewed by the camera will show the contour of the bottle totally dark and with such sharp image as the camera is able to reproduce. Further, the image of the liquid container will be free of perspective distortions, as clearly demonstrated by the test images shown in FIGS. 6 and 7.

The reason for the perfect, dark outline is as follows. Without any article located between the lenses 2, 3 the camera field of view will be filled by light from the light source 1, i.e. causing the image to be completely bright. If some part of that light is deflected relative to its normal direction, that part of the light will not reach the camera lens 4', and those portions will become dark. This is in particular the situation with a transparent bottle of glass or plastics. The material of such bottles will refract the light to cause it to change direction. Such refraction is in particular strong at the outline, which therefore appears to be dark. The more thick walled bottle present, the wider the dark outline. A glass bottle having a somewhat thick wall will in most cases appear to be dark all over. Even quite thin walled bottles of plastics provide a sharp and excellent outline. As clearly demonstrated by the test images shown in FIGS. 6 and 7, it is noted that the glass bottle shown in FIG. 6 appears with a bottle cross section which is folly dark, whereas the bottle of plastics shown in FIG. 7 a appears with a sharp and excellent outline but has some brighter portions between the left and right outline.

The reason why the image will be free of perspective distortions is that the liquid container is in a space or field of light having parallel light rays provided by the lenses 2, 3. The liquid container is therefore capable of providing a shadow which is a plane projection view onto a plane normal to the optical axis, i.e. the plane of the lens 3 as shown in the example of FIG. 1. A plane projection of a body has no perspective distortion.

The sensitivity of the contour or outline imaging can be expressed as minimum light deflection which provides shadow in the image. Increased sensivity implies that more thin walled articles provide excellent dark outline. The sensitivity of the arrangement will increase with reduced size of the light source, and with reduced size of the input pupil of the camera lens 4'.

A rather practical limitation in the arrangement is that lenses, such as Fresnel lenses, have substantial lens errors, a feature which can reduce that field of view which can be used in practice. It could of course be envisaged to use corrected, conventional collimator lenses. Such technique could be used in extremely sensitive arrangements. However, as lens diameters of 40 centimetres or somewhat more is normally required for inspecting bottles and other liquid containers, the size and weight of such conventional collimator lenses in an arrangement according to the present invention would be impractical, and the cost thereof would be excessive. Thus, although the present invention discloses the use of Fresnel lenses, it would lie within the scope of the present invention and within that obvious to an expert in the art to use means other than Fresnel lenses for directing light rays. Such other means for light path controlling could e.g. be conventional collimating optical element, such as a common type optical lens or a holographic element. Thus, although Fresnel lenses are considered to constitute an important element in the preferred embodiment of the present invention, technically equivalent means yielding the same end result could be used.

An important and interesting feature of the present invention is the light source 1. A great advantage of the present arrangement is light-efficiency. According to a proto-type of the invention, it has been discovered that a single light emitting diode is an ideal and preferred light source, for the embodiments shown in FIGS. 1–4, 5, 8, 10 and 11. It has further been shown according to the invention, that such light emitting diode (LED) provides more than sufficient light for a TV camera of the CCD type, related types of cameras, or other types of light sensitive elements. A light emitting diode has a limited light spectrum. That reduces the effect of chromatic defects in the lenses, in particular in Fresnel lenses, something which is otherwise one of the great lens defects of such Fresnel lenses. A further advantage of using such type of light source is that its operation can be easily controlled, e.g by pulsing the light emitting diode. By synchronizing the pulsing to the camera image frequency, it is possible to remove any effect on the image caused by movement.

In practice, an arrangement as shown in FIG. 1 could be considered as bulky. It is therefore possible by the use of simple means to provide a much more compact arrangement. That is further illustrated in FIG. 8. Only a small part of the faces of the Fresnel lenses need to be used. Thus, a substantial part of the Fresnel lenses 2,3, as shown in FIG. 1, could be removed, e.g. to let the Fresnel lenses 2,3 have a rectangular shape.

Figure 8:
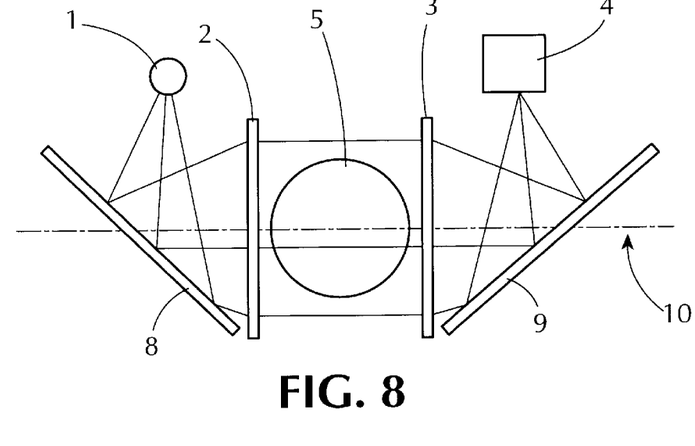
FIG. 8 illustrates a modification of the embodiment according to FIG. 1.

Further, it is possible by means of two mirrors 8, 9 located at an angle, e.g. 45° to a common central axis 10 through said lenses to convey light between said light source 1 and the lens 2, and to convey light not refracted or hidden by said container between the lens 3 and the camera 4, as clearly shown in FIG. 8. However, the length of the total optical axis of the lenses will not be reduced. When locating an arrangement as shown in FIG. 8 in a cabinet for such device for generating, detecting and recognizing the contour image of a liquid container, it will be readily appreciated by the expert in the art that the arrangement must be adapted according to customer specifications.

Figure 2:
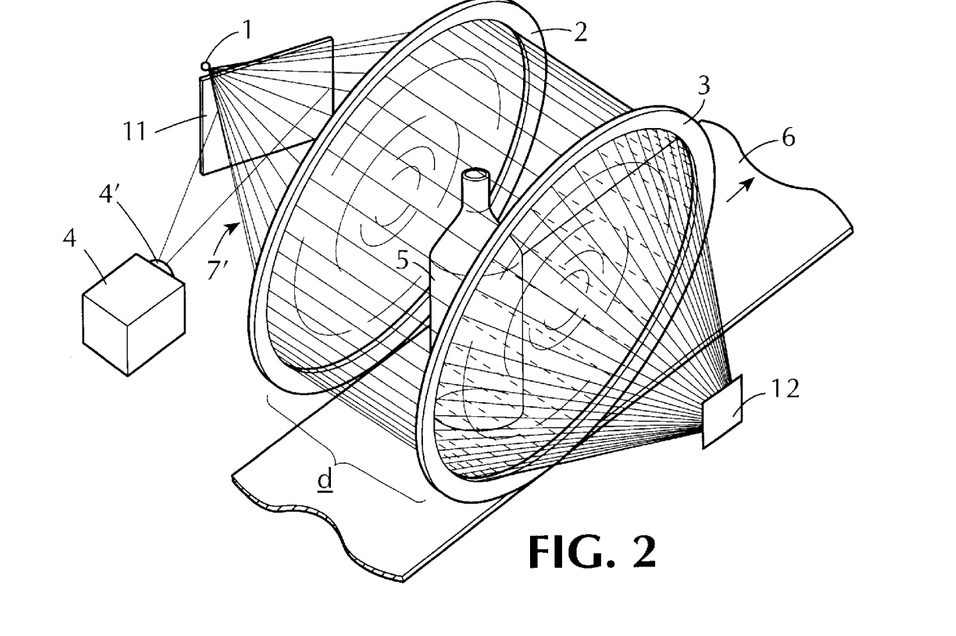
FIG. 2 shows a second embodiment of the device according to the present invention.

In the second embodiment of FIG. 2 the light source 1, e.g. a light emitting diode emits light via a semi-transparent, inclined mirror 11 towards a first lens 2, suitably of Fresnel lens type. The light source is located at the focal point of said first lens 2. The light rays 7' received by the lens 2 are directed across the path of the liquid container 5 as parallel light rays. At the other longitudinal side of the conveyor 6 there is located a second lens 3, suitably of Fresnel lens type, and spaced therefrom at some distance from the focal point of the lens 3 there is located a retro-reflector means 12, the property of which is to direct received light rays back in the exact same direction as received.

Light rays which are not hidden or deflected by the liquid container 5 will thus be reflected by the retro-reflector means 12 back through the lenses 2 and 3 and onto the mirror 11 which is located at an angle, suitably 45°, relative to the common optical axis of lenses 2, 3 on which axis the light source 1 is located, and then deflected by the mirror 11 onto the detector 4 located at optical focal point of lens 2. Thus, the retro-reflected light rays which have passed through the lenses 2, 3 will reach the inclined mirror 11 and he deflected therefrom onto the lens 4' of the camera 4.

In the embodiments of the invention and the light source 1, e.g. a LED would preferably have the possibility of having its operation controlled, e.g. by synchronizing its operation with container location relative to the lenses, or by pulsing the light source synchronously to camera image frequency.

Thus, a major advantage of the embodiment of FIG. 2 is through the use of a light source such as a light emitting diode 1 in combination with the Fresnel lenses 2, 3, thus compensating for the inherent chromatic defects of a Fresnel lens.

Figure 3:
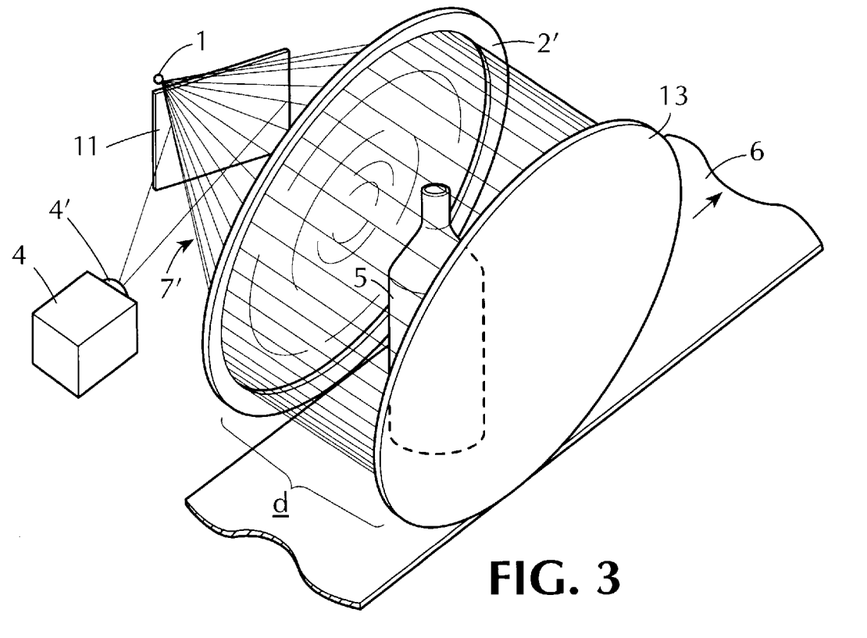
FIG. 3 shows a third embodiment of the present invention.

The third and preferred embodiment of the present invention is now to be described with reference to FIG. 3, in which the light source 1, e.g. a light emitting diode emits light via a semi-transparent, inclined mirror 11 towards a single lens 2', suitably of Fresnel lens type. The light source 1 is located at the focal point of the lens 2'. The light rays 7' received by the lens 2' are directed across the path of the liquid container 5 as parallel light rays. At the other longitudinal side of the conveyor 6 there is located a light reflecting means 13 in the form of a planar mirror having conventional reflection properties. The mirror is located orthogonally to the axis through lens 2', i.e. parallel to said lens 2'.

Light rays which are not hidden or deflected by the liquid container 5 will thus be reflected by mirror 13 back as parallel rays 14 towards lens 2', pass through lens 2' and the bundle of rays will converge, then be reflected by mirror 11 which is located at an angle, suitably 45°, relative to the optical axis of lens 2' on which axis the light source 1 is also located, and then be deflected by mirror 11 onto the detector 4 located at optical focal point of lens 2'.

Figure 4:
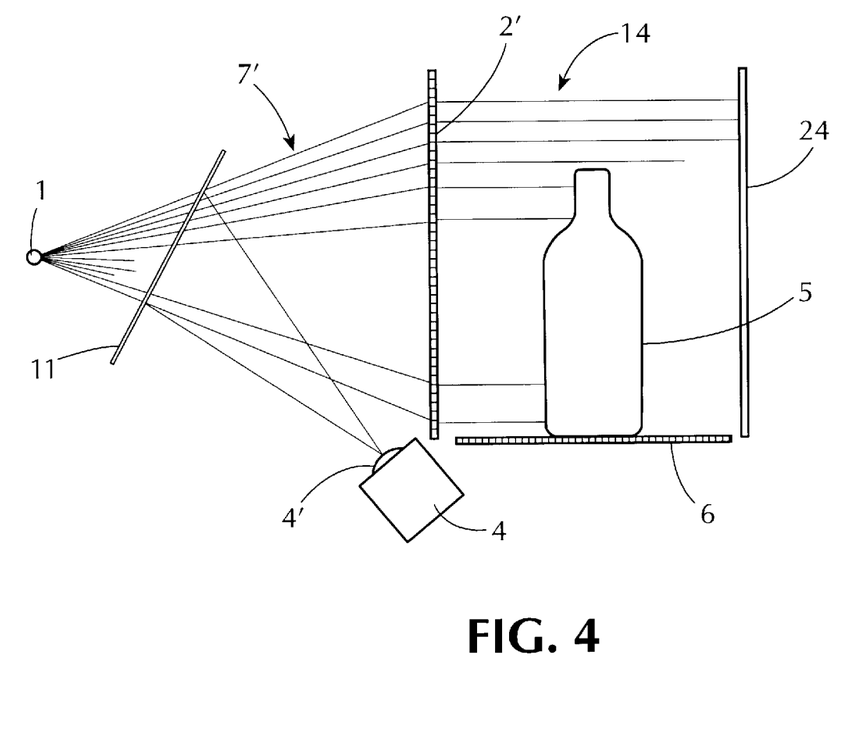
FIG. 4 shows a fourth embodiment of the present invention.

The fourth embodiment of the present invention is now to be described with reference to FIG. 4, in which the light source 1, e.g. a light emitting diode emits light via a semi-transparent, inclined mirror 11 towards a single lens 2', suitably of Fresnel lens type. The light source 1 is located at the focal point of the lens 2'. The light rays 7' received by the lens 2' are directed across the path of the liquid container 5 as parallel light rays. At the other longitudinal side of the conveyor 6 there is located a light reflecting means 24 in the form of a retro-reflector having conventional retro-reflective properties. The retro-reflector is located orthogonally to the axis through lens 2', i.e. parallel to said lens 2'.

Light rays which are not hidden or deflected by the liquid container 5 will thus be retro-reflected by retro-reflector 24 back as parallel rays 14 towards lens 2', pass through lens 2' and the bundle of rays will converge, then be reflected by mirror 11 which is located at an angle, suitably 45°, relative to the optical axis of lens 2' on which axis the light source 1 is also located, and then be deflected by mirror 11 onto the detector 4 located at optical focal point of lens 2'.

The various embodiments have advantages and disadvantages.

The first and third embodiments, which do not use the properties of retro-reflective means, have the advantage that when all elements are properly aligned, the measurement area will have an evenly distributed illumination, thus yielding a completely geometrically correct measurement geometry (no perspective errors). Thus those embodiments are self-controlling. The disadvantage is the proper alignment to obtain an evenly distributed illumination.

The second and fourth embodiments have more or less the same advantages and disadvantages as found for the first and fourth embodiments. One major advantage is, however, that the embodiments are self-aligning, i.e. the light received by the retro-reflector 24 or 24' will return along exactly the same path as received. Thereby, it is always obtained a complete and evenly distributed illumination of the measurement area, even though camera and light source are not located at the focal point of the lens 2' or 2.

Figure 10:
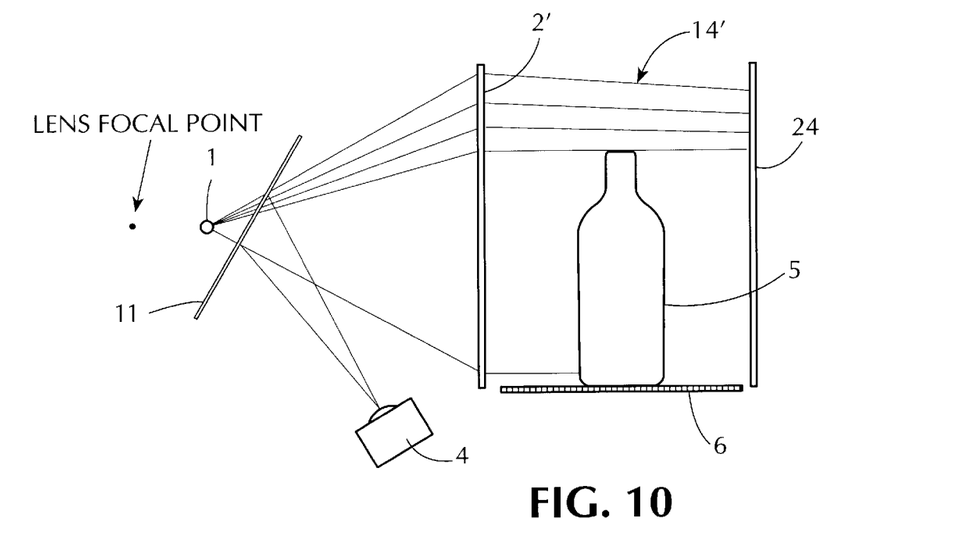
FIGS. 10 and 11 are slight modifications of the fourth and second embodiments, respectively.
Figure 11:
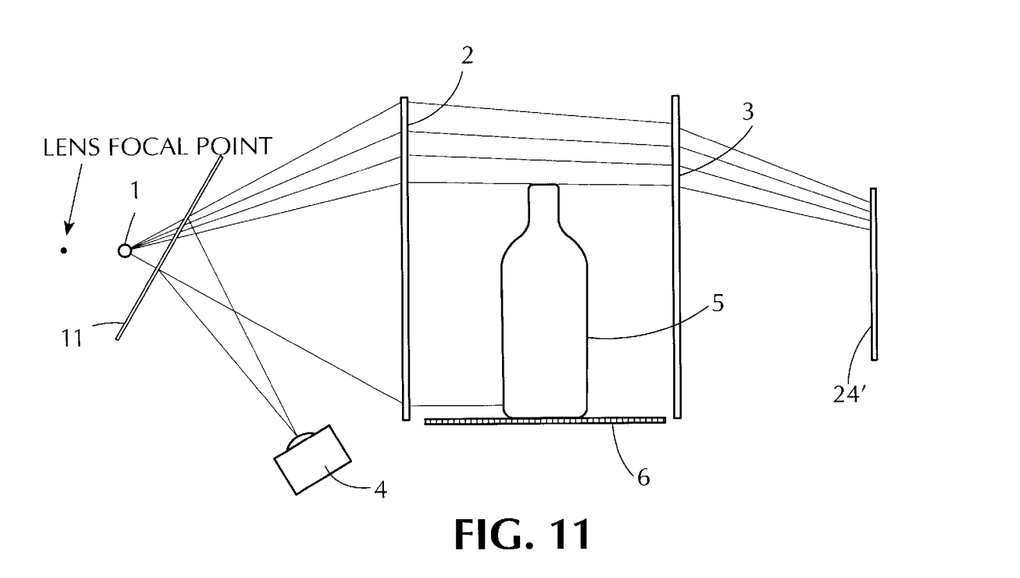

However, as clearly demonstrated on FIG. 10 and 11, if the light source 1 and the camera 4 are not located at the focus of lens 2' or 2, geometrical error will be created due to perspective errors. The light 14' will not pass across the path 6 as parallel rays at the location where the object, such as a bottle, is present. Thus, the embodiments are self-adjusting, but not self-controlling.

In the embodiment of FIG. 2, it is considered disadvantageous to locate the retro-reflector 24 at the focal point of lens 3, due to microstructure properties of typical retro-reflectors. Locating the retro-reflector at the focal point of lens 3 would cause a rather intense reflected spot, however, with an enlarged version of the microstructure superimposed on the light distribution directed back from the retro-reflector to the camera.

Figure 5:
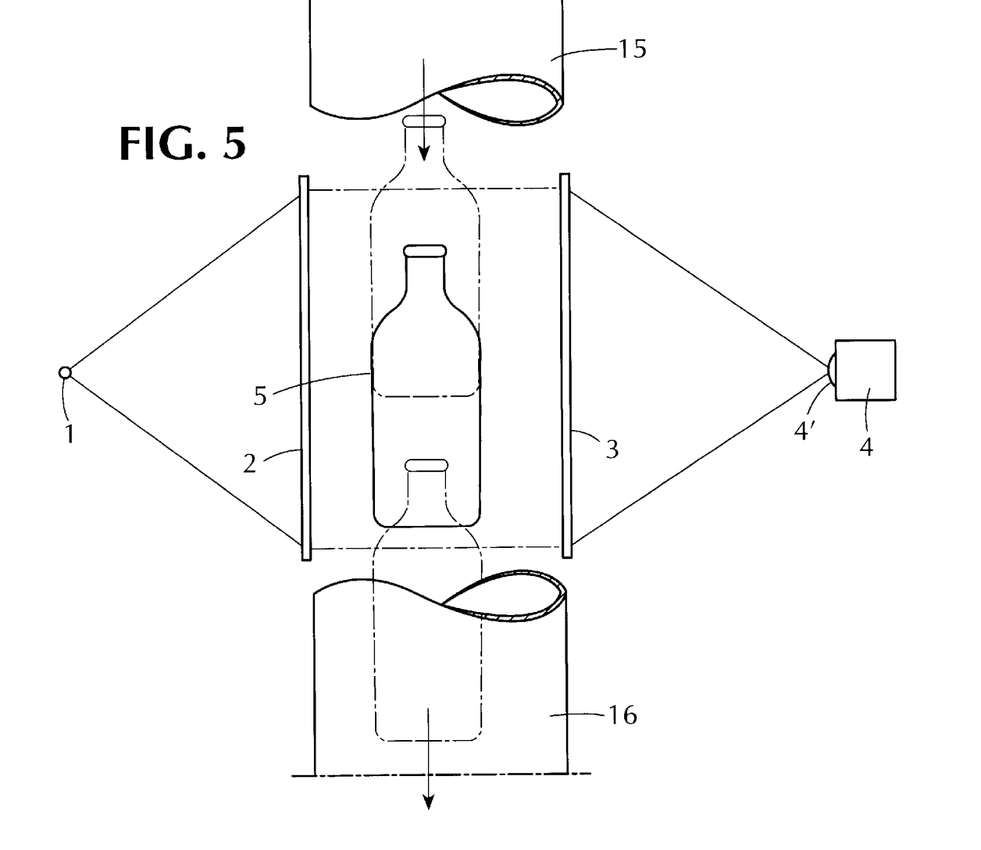
FIG. 5 shows a modification of the embodiments of the present invention in connection with a free fall of a liquid container.

In FIG. 5 there is illustrated an application of the present invention which could be used for any of the embodiments discussed and shown in connection with FIGS. 1, 2, 3 and 4, subject to some modification. For the sake of explaining the application of the present invention in connection with the embodiment of FIG. 5, there is suitably made a reference to that which has been described and disclosed in connection with FIG. 1. Thus, there is, as in the embodiment of FIG. 5 a light source 1, lenses (e.g. Fresnel lenses) 2, 3, and a camera 4 with a camera lens 4' Installed in the camera 4.

FIG. 5 is included to illustrate means for enabling the liquid container path of travel to be a free fall path, at least past the image generating, detecting and recognizing arrangement as shown. Thus, there is provided an upper guide duct 15 and lower guide duct 16. Although not specifically shown on FIG. 5, it should be readily appreciated by the expert in the art that the said ducts 15 and 16 together with the lenses 2, 3 and side panels (not shown) adjacent said lenses 2, 3 (and not interfering with the light rays between the lenses 2, 3) could form an uninterrupted guide duct for the liquid container 5 during its passage from the upper duct part 15 to the lower part duct 16, although the cross section of such duct inherently would be slightly different at the section of the arrangement spanned by the lenses 2, 3.

Thus, the embodiment of FIG. 5 clearly demonstrates how the complete liquid container, and in particular the bottom thereof may be inspected by the camera 4 without any obstructions e.g. caused by a conveyor 6 on which such liquid container is located during its travel, as e.g. shown in FIGS. 1–4, and 10, 11.

Finally, the invention is to be described in connection with the enclosed FIG. 9. The light source 1 is connected to processing means 17 which includes synchronizing means 18 for any required synchronized operation of the light source, such as synchronizing with container location relative to the lens(es) (e.g. Fresnel lenses), or pulsing synchronously to camera image frequency (light detector means 4). The light detector means, suitably in the form of the camera 4 connects with the processing means 17. Further, there is included comparing means 19 capable of comparing an image detected by the light detector means 4 and processed by the processing means 17 to recognize a contour image of a particular container and communicating such recognition back to the processing means 17 in order to operate by means of the processing means 17 a display 20 and/or a printer 21. A control panel 22 may suitably be provided in order to set anyone of said processing means 17, synchronizing means 18, comparing means 19, display 20 or printer 21. The data displayed and printed could include identification of a particular container detected and/or its possible redemption value, although in principle any type of data relevant to the recognition could be displayed and/or printed.

Further, a power supply 23 is provided for delivering power via said processing means 17 to said light source 1, said processing means 17, said synchronizing means 18, said container conveyor means 6; 15, 16, said light detector 4, said comparing means 19, said display 20, said printer 21 and said control panel 22.

Figure 9:
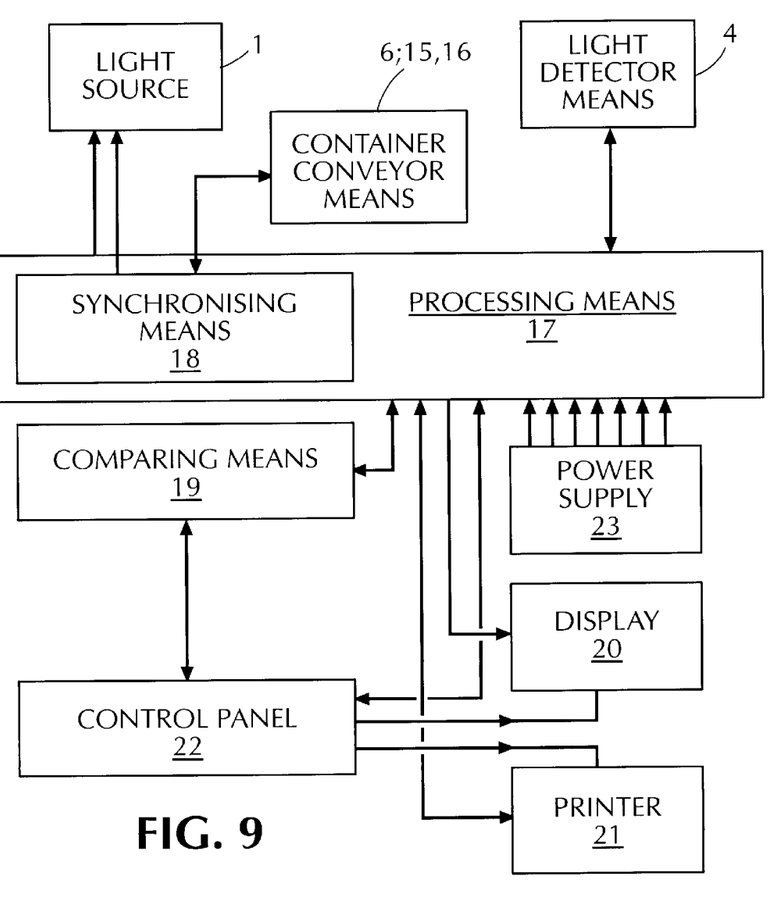
FIG. 9 is a block schematic over the overall system for operating the device, according to the present invention.

It will be obvious to an expert in the art that the layout of the overall system as shown in FIG. 9, could be modified in any suitable way without departing from the scope and spirit of the present invention.

Further, the embodiments shown and described in the present specification are only intended to illustrate the present invention without necessarily limiting the scope thereof. Thus, any modification of the embodiments and any technical equivalents which would lie with the spirit and scope of the present invention could be envisaged.

I claim:

1. A device for generating, detecting and recognizing a contour image of a liquid container, such as at least partly transparent, coloured or non-coloured bottles, comprising a stationary light source which emits scattered light, light detector means, a container inspection region illuminated by said light source and inspected by said light detector means, means for conveying a container in a substantially continuous motion along a path into and out of the inspection region, means for directing said scattered light received from said light source as parallel rays transversely of the path travelled by said container, a planar mirror for receiving such parallel light rays which are not refracted or hidden by said container, and reflecting such received parallel light rays back as parallel rays transversely of said path and through said directing means, said means for directing light rays being a single Fresnel lens, being located on one side of said inspection region and at a first longitudinal side of said path, and said planar mirror being located at a second longitudinal side of said path, said Fresnel lens and said planar mirror defining said inspection region, said Fresnel lens having a light receiving area, said light source being located on said one side of said inspection region and capable of emitting said scattered light towards said Fresnel lens over substantially the entire light receiving area of said Fresnel lens to provide a field of light to said Fresnel lens, inclined mirror means located on said one side of said inspection region for receiving and redirecting said reflected light rays passing through said Fresnel lens, to be received by the light detector means, said inclined mirror means being a semi-transparent mirror capable of passing through light rays emitted by said stationary light source towards said single Fresnel lens, said light detector means located on said one side of said inspection region for receiving said redirected light, said light detector means being a TV camera capable of detecting a container contour highlighted by light not refracted or hidden by the container, processing means connected to said light detector means for processing signals from said detector means which are indicative of such detected light rays, and means for comparing such processed signals with predetermined container feature data to recognize said contour image of a container.

2. A device according to claim 1, wherein said light source is elected from the group of a light emitting diode, an incadescent lamp; an arc lamp means; and a laser source having a light diffusor means.

3. A device according to claim 1, wherein said TV camera is a CCD camera.

4. A device according to claim 1, wherein said light source is a pulsed light source.

5. A device according to claim 2, further comprising means for synchronizing operation of said light source with container location relative to the inspection region.

6. A device according to claim 4, including means for pulsing said light source synchronously to camera image frequency.

7. A device according to claim 1, further comprising means for enabling said container path of travel to be a free fall path.

8. A device according to claim 1 wherein said light source is located at the focus of said Fresnel lens.

9. A device according to claim 1 wherein said semi-transparent mirror is positioned in front of said light source and said light detector means has a camera lens that is out of alignment with the Fresnel lens.

* * * * *

UNITED STATES PATENT AND TRADEMARK OFFICE
CERTIFICATE OF CORRECTION

PATENT NO : 5,898,169
DATED : April 27, 1999
INVENTOR(S) : Andreas NORDBRYHN

It is certified that error appears in the above-identified patent and that said Letters Patent is hereby corrected as shown below:

In column 2, line 1, change "ant" to --and--

In column 3, line 2, change "rot" to --not--

In column 3, line 44, change "Sears" to --means--

In column 3, line 46, change "Pears" to --means--

In column 6, line 3, change "folly" to --fully--

Figure 7:
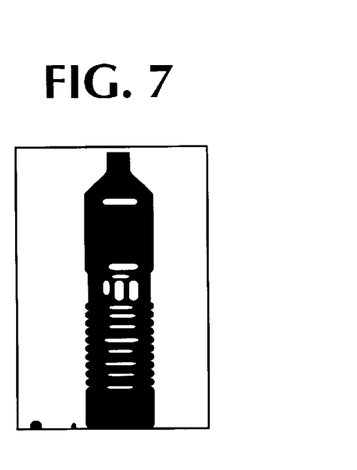
FIG. 7 is a test picture of a further bottle image generated and detected according to the principles of the embodiment of FIG. 1.

In column 6, line 4, after "Fig. 7" delete --a--

Signed and Sealed this

Ninth Day of November, 1999

Q. TODD DICKINSON

*Attest:*

*Attesting Officer*          Acting Commissioner of Patents and Trademarks